United States Patent [19]

Swearingen et al.

[11] Patent Number: 5,105,033
[45] Date of Patent: Apr. 14, 1992

[54] PROCESS FOR PREPARING 1,1-DICHLORO-1-FLUOROETHANE

[75] Inventors: Steven H. Swearingen; John F. Wehner; Marlin G. Ridley, all of Wilmington, Del.

[73] Assignee: E. I. Du Pont de Nemours and Company, Wilmington, Del.

[21] Appl. No.: 738,679

[22] Filed: Jul. 31, 1991

Related U.S. Application Data

[63] Continuation of Ser. No. 356,949, May 25, 1989, abandoned.

[51] Int. Cl.$^5$ .................. C07C 17/00; C07C 17/38
[52] U.S. Cl. .................. 570/166; 570/168; 570/177
[58] Field of Search .................. 570/166, 168, 177

[56] References Cited

U.S. PATENT DOCUMENTS 3,755,477  8/1973  Firth et al. ............... 260/653.4
3,836,479  9/1974  Pauckeh et al. .
4,258,225  3/1981  Feiring ..................... 570/168

FOREIGN PATENT DOCUMENTS 2013675  10/1990  Canada ..................... 260/658.2
353059   7/1989   European Pat. Off. ......... 19/8
2739478  3/1978   Fed. Rep. of Germany ...... 570/166

OTHER PUBLICATIONS

*Journal of Flourine Chemistry*, vol. 14 (1979), pp. 7–19.

Primary Examiner—Alan Siegel

[57] ABSTRACT

A manufacturing process is disclosed for preparing 1,1-dichloro-1-fluorethane by the addition of hydrogen fluoride to 1,1-dichloroethylene in the presence of a hydrofluorination catalyst providing 1,1-dichloro-1-fluoroethane in high yields and reduced 1,1-dichloroethylene content.

Additionally, a process is disclosed for reducing the 1,1-dichloroethylene content of a mixture of 1,1-dichloroethylene and 1,1-dichloro-1-fluoroethane.

22 Claims, No Drawings

PROCESS FOR PREPARING 1,1-DICHLORO-1-FLUOROETHANE

This is a continuation of application Ser. No. 07/356,949, filed May 25, 1989 now abandoned.

FIELD OF THE INVENTION

A manufacturing process for preparing 1,1-dichloro-1-fluoroethane by the addition of hydrogen fluoride to 1,1-dichloroethylene in the presence of a hydrofluorination catalyst to provide 1,1-dichloro-1-fluoroethane in high yields and with reduced 1,1-dichloroethylene content.

BACKGROUND OF THE INVENTION

Concerns over the possible role of certain chlorofluorocarbons (CFC's) in the depletion of the stratospheric ozone layer have increased interest in developing hydrogen-containing chlorofluorocarbons (HCFC's) which are believed to have little or no ozone depletion potential.

One such alternative HCFC which may be used as a solvent, such as in cleaning electronic circuit boards, as a blowing agent for the manufacture of polymer foams, as an aerosol propellant and the like and which is expected to have little effect upon the stratospheric ozone layer is 1,1-dichloro-1-fluoroethane ($CH_3CCl_2F$, HCFC-141b), a compound which has an atmospheric boiling point of about 32° C.

1,1-Dichloro-1-fluoroethane is a known compound which has been prepared by a number of known methods. One such method is by the halogen exchange reaction of 1,1,1-trichloroethane with hydrogen fluoride, usually in the presence of a halogen exchange catalyst. Such a reaction may be represented by Equation I,

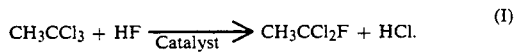
$$CH_3CCl_3 + HF \xrightarrow{Catalyst} CH_3CCl_2F + HCl. \quad (I)$$

While the reaction as shown in Equation I proceeds very readily, there are several disadvantages to the reaction if it were to be used industrially. One such disadvantage is that, for each molecule of 1,1-dichloro-1-fluoroethane produced, one molecule of hydrogen chloride is also generated which must be recovered and disposed of.

Another reaction to prepare 1,1-dichloro-1-fluoroethane involves hydrogen fluoride addition to 1,1-dichloroethylene (vinylidene chloride) as represented by Equation (II).

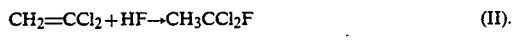
$$CH_2=CCl_2 + HF \rightarrow CH_3CCl_2F \quad (II).$$

The reaction as represented by Equation (II) appears to be ideal for the preparation of 1,1-dichloro-1-fluoroethane provided high yields of 1,1-dichloro-1-fluoroethane are achieved, and the vinylidene chloride is effectively consumed. Note that, in this reaction, hydrogen chloride is not formed. High conversion of vinylidene chloride is necessary since both 1,1-dichloro-1-fluoroethane and vinylidene chloride boil at around 32° C., and separation of these two compounds by conventional methods, such as by distillation, is almost impossible.

In U.S. Pat. No. 3,755,477, Firth et al. disclose a vapor-phase reaction of vinylidene chloride with hydrogen fluoride in the presence of a steam-treated chromium oxide catalyst. The disclosure indicates that, at 70°-80° C. reaction temperature, 45 percent of the fluorinated products was 1,1-dichloro-1-fluoroethane while the remainder were more highly fluorinated products, namely, 1-chloro-1,1-difluoroethane and 1,1,1-trifluoroethane. At 90°-100° C. reaction temperature, no 1,1-dichloro-1-fluoroethane was reported to be produced.

In U.S. Pat. No. 3,836,479, Paucksch et al. disclose the preparation of a high surface area aluminum fluoride catalyst by admixing boron oxide with alumina, shaping the mixture and thereafter treating the shaped catalyst with hydrogen fluoride. The thus-prepared catalyst is claimed to be of high activity in catalyzing the hydrogen fluoride addition to double or triple bond compounds. Paucksch et al. teach at Col. 5, lines 35-51, that the claimed catalysts are especially active in hydrogen fluoride addition to olefins which contain one or more fluorine atoms, such as vinyl fluoride, vinylidene fluoride or tetrafluoroethylene, the reaction starting without any external heat and that, at 40°-100° C., 100% conversion to hydrofluorinated compounds is obtained. However, when the olefin contains chlorine or bromine, such as trichloroethylene, 1,1-dichloroethylene, tribromoethylene or 1,1-dibromoethylene, reaction temperatures of between 150° C. to 500° C. are necessary. This teaching is illustrated in Examples 12-15 which show that, while the reaction of hydrogen fluoride with vinyl fluoride, vinylidene fluoride or tetrafluoroethylene proceed with 100% conversion of the olefins at 55°-60° C., the hydrogen fluoride addition to vinyl chloride required a temperature of 175° C. with only 28% conversion of vinyl chloride.

In U.S. Pat. No. 3,803,241, Stolkin et al. disclose a hydrofluorination catalyst prepared by impregnating vacuum-dried alumina with a chromium salt solution and then activating with a stream of hydrogen fluoride at a temperature below 250° C. Preparative reactions are carried out with excess hydrogen fluoride at 140°-400° C. In Example 1 it is shown that, by the use of this catalyst in the vapor-phase reaction of vinylidene chloride and hydrogen fluoride at 198° C., the product obtained was 98.8 volume-percent 1,1,1-trifluoroethane and only 0.2 volume-percent 1,1-dichloro-1-fluoroethane.

In U.S. Pat. No. 3,904,701, Schultz et al. disclose a hydrofluorination catalyst prepared as in the above cited U.S. Pat. No. 3,803,241 with the exception that the alumina, before treatment with hydrogen fluoride, is impregnated with a bismuth salt solution. In Example 1 the claimed catalyst is used in the vapor-phase reaction of hydrogen fluoride with vinylidene chloride, the reaction temperature being 198° C. to 210° C. The products obtained consisted of 99.7 volume-percent $CH_3CF_3$, 0.2 volume-percent $CH_3CF_2Cl$ and 0.1 volume-percent unreacted $CH_2=CCl_2$. The presence of 1,1-dichloro-1-fluoroethane is not mentioned.

In U.S. Pat. No. 4,147,733, Fiske et al. disclose a vapor-phase reaction of aqueous hydrogen fluoride with vinylidene chloride in the presence of a metal fluoride catalyst, which is an admixture of aluminum fluoride, chromium fluoride and nickel fluoride, at 250° C. to 415° C. wherein conversion of vinylidene chloride to fluorinated products is extremely low—2% at 250° C. and 13.5% at 415° C. There is no mention of 1,1-dichloro-1-fluoroethane as one of the products formed.

It is an object of the present invention to provide a manufacturing process for 1,1-dichloro-1-fluoroethane. It is a further object of the invention to provide a process for the preparation of 1,1-dichloro-1-fluoroethane by the addition of hydrogen fluoride to 1,1-dichloroethylene providing said 1,1-dichloro-1-fluoroethane in high yields. It is still a further object of the invention to provide a process for the preparation of 1,1-dichloro-1-fluoroethane by the addition of hydrogen fluoride to 1,1-dichloroethylene in the presence of an aluminum fluoride catalyst to provide said 1,1-dichloro-1-fluoroethane in high yields and substantially free of 1,1-dichloroethylene. Another object to provide a process for reducing the 1,1-dichloroethylene content of mixtures of 1,1-dichloroethylene and 1,1-dichloro-1-fluoroethane.

SUMMARY OF THE INVENTION

This invention provides a process for preparing 1,1-dichloro-1-fluoroethane comprising the steps of (a) contacting a vapor phase mixture of 1,1-dichloroethylene and substantially anhydrous hydrogen fluoride with a hydrofluorination catalyst to produce a first product stream containing 1,1-dichloro-1-fluoroethane and 1,1-dichloroethylene and, thereafter, (b) contacting said first product stream with substantially anhydrous hydrogen fluoride at an effective temperature and pressure wherein at least some of the first product stream is in the liquid state to form a second product stream, and (c) recovering 1,1-dichloro-1-fluoroethane with reduced 1,1-dichloroethylene content from the second product stream.

The first contacting step can be maintained at a temperature of from about 25° C. to about 150° C. and a pressure of from about atmospheric to about 160 psig, and the second contacting step can be at a temperature of about 5° C. to about 75° C. and a pressure of from about atmospheric to about 80 psig.

Also, a process has been discovered for reducing the 1,1-dichloroethylene content of a mixture of 1,1-dichloroethylene and 1,1-dichloro-1-fluoroethane comprising contacting said mixture with substantially anhydrous hydrogen fluoride at an effective temperature and pressure wherein at least some of the mixture is in the liquid state to form a product stream, and recovering 1,1-dichloro-1-fluoroethane with reduced 1,1-dichloroethylene content from the product stream.

DETAILS OF THE INVENTION

The present invention process provides very high yields of 1,1-dichloro-1-fluoroethane with minimal formation of polyfluorinated products, high boilers or tars and with very high conversion of 1,1-dichloroethylene. This high conversion of 1,1-dichloroethylene is most important since 1,1-dichloro-1-fluoroethane and 1,1-dichloroethylene have almost identical boiling points (atmospheric boiling point of 32° C.), and thus it is virtually impossible to separate them by conventional means, such as by distillation.

The catalyst used in the present process is a hydrofluorination catalyst. By hydrofluorination catalyst is meant any compound which promotes the addition of hydrogen fluoride to the starting olefin of the present invention. Such compounds can be any class of metal fluoride, neat or impregnated on a suitable substrate, including fluorides of aluminum, zinc, tin, iron, cobalt, magnesium, zirconium, nickel, etc.

Preferably, the hydrofluorination catalyst may be an aluminum fluoride catalyst. By aluminum fluoride catalyst is meant an aluminum fluoride which may be used in hydrogen fluoride addition to unsaturated compounds or in halogen exchange reactions of halocarbons with hydrogen fluoride. The catalyst can be prepared by treating any aluminum-containing compound capable of being converted to aluminum fluoride by contacting the compound with a vaporizable fluorine-containing compound such as HF, $SF_4$, $CCl_3F$, $CCl_2F_2$, $CHF_3$ or $CCl_2FCClF_2$. By vaporizable fluorine-containing compound is meant a compound which, when passed over the aluminum-containing compounds, will convert the aluminum-containing compound to essentially aluminum fluoride. Preferably, the vaporizable fluorine-containing compound is hydrogen fluoride.

For example, the catalyst useful in the practice of this invention can be prepared by treating aluminum chloride, aluminum bromide or alumina with hydrogen fluoride until the aluminum chloride, aluminum bromide or alumina is converted essentially into aluminum fluoride. Alumina is preferred. It is recognized that, in the act of such a treatment, conversions are usually not complete, that is, there may be some chloride or bromide left when the aluminum fluoride is prepared from aluminum chloride or aluminum bromide, or when prepared from alumina, there may be some oxyfluorides or hydroxyfluorides present. The procedure generally used to prepare the aluminum fluoride catalyst is to treat aluminum chloride, aluminum bromide or alumina with hydrogen fluoride which is initially diluted with a dry inert gas such as nitrogen and, thereafter, to increase the concentration of hydrogen fluoride until 100% hydrogen fluoride is used. The treatment temperature may be raised to facilitate the conversion, say, up to about 500° C. Aluminum chloride or aluminum bromide is usually converted to aluminum fluoride very readily so that high temperatures are not necessary; high temperatures are undesirable with aluminum chloride because of its tendency to sublime. An aluminum fluoride catalyst may also include minor amounts of other metal fluorides admixed therein, such as fluorides of nickel, chromium, cobalt and the like. Such aluminum fluorides containing other metal fluorides are usually prepared by impregnating alumina with appropriate metal salt solutions, followed by drying and treatment with hydrogen fluoride as described. The term "aluminum fluoride catalyst" as used herein, and in the appended claims include normal aluminum fluorides which may contain some chlorofluorides, bromofluorides, oxyfluorides, hydroxyfluorides as well as minor amounts of other metal fluorides.

In the usual procedure of the present invention, a mixture of hydrogen fluoride and 1,1-dichloroethylene, in the vapor phase, is introduced into a first contacting step to pass over or through an aluminum fluoride catalyst which may be preformed or formed in situ in the reactor by procedures such as those described above. The product stream (first product stream) from this first contacting step then undergoes a second contacting step also with an aluminum fluoride catalyst. The product stream from the second contacting step (second product stream) is usually 1,1-dichloro-1-fluoroethane of very high yield and purity, up to 99.5%, with a minor amount of 1-chloro-1,1-difluoroethane and minimal amounts of 1,1-dichloroethylene, which may be some few hundred parts per million.

The second contacting step must be at an effective temperature and pressure such that at least some of the first product stream is in the liquid state. By effective temperature and pressure is meant the combination of temperature and pressure in the second contacting step which causes the first product stream to be at least partially in the liquid state in this second contacting step to form a second product stream. The first contacting step and the second contacting step may occur in the same or different reactors or overlap between reactors.

In the first contacting step, the reaction of 1,1-dichloroethylene and hydrogen fluoride in the presence of an aluminum fluoride catalyst can be carried out at a temperature of from about 25° C. to about 150° C., preferably from about 50° C. to about 100° C., more preferably from about 55° C. to about 95° C. Since the reaction between 1,1-dichloroethylene and hydrogen fluoride in the presence of an aluminum fluoride proceeds exothermically, any well-known means to control the temperature in the reactor may be provided. The pressure in the first contacting step is not critical and may be atmospheric or superatmospheric, but for convenience, pressures of from atmospheric to about 160 psig may be used, preferably from about atmospheric to about 50 psig. The product stream from the first contacting step whose organic products comprise, usually, from about 90% to about 95% 1,1-dichloro-1-fluoroethane, about 0.1% to 1% 1-chloro-1,1-difluoroethane and about 0.1% to 8% 1,1-dichloroethylene is introduced into the second contacting step to contact substantially anhydrous hydrogen fluoride and an aluminum fluoride catalyst.

The reaction temperature in the second contacting step may be from about 5° C. to about 75° C., preferably about 25° to about 75° C., and the pressure may be from about atmospheric to about 80 psig, preferably from about 35 to about 50 psig. Higher pressures may be used but may increase costs without yielding corresponding advantages. The reaction temperature and the pressure in the second contacting step are so chosen that at least a portion of the product stream in the second contacting step is in the liquid state. Thus, since 1,1-dichloro-1-fluoroethane and 1,1-dichloroethylene both have atmospheric boiling points of 32° C., with the reactor at atmospheric pressure, any reaction temperature below about 30° C. will provide at least a portion of the reactants in liquid state. Similarly, if the reactor pressure is 45 psig, any reaction temperature below about 65° C. will provide the reactants in liquid state. The preferred combinations of temperature and pressure are temperatures in the range of from about 55° C. to about 75° C. and pressures in the range of from about 30 psig to about 75 psig.

The temperatures in the contacting steps may be uniform throughout or may vary as the product stream proceeds through the contacting steps. The pressures in the first contacting step and in the second contacting step may be the same or different provided that the reaction temperature and the pressure in the first contacting step are such that the reactants are initially present in the vapor phase, and in the second contacting step, are such that at least a portion of the reactants in the second contacting step is in liquid phase.

The amount of hydrogen fluoride relative to the amount of 1,1-dichloroethylene in the reactant mixture in the first contacting step is not critical, but to enhance catalyst activity, it may be at least stoichiometric, i.e., one mole of hydrogen fluoride per mole of 1,1-dichloroethylene. For increased conversions, a higher ratio of hydrogen fluoride to 1,1-dichloroethylene is preferably used, say, from about 1 to about 15, more preferably from about 1.3 to about 8, and most preferably from about 1.3 to about 2.5 moles of hydrogen fluoride per mole of 1,1-dichloroethylene. Additionally, if desired, particularly when the hydrogen fluoride to 1,1-dichloroethylene ratio is relatively low, say from about 2 to 2.5 in the first contacting step, an additional amount of hydrogen fluoride may be introduced into the second contacting step along with the product stream from the first contacting step. Hydrogen fluoride used in the present process can be commercially available anhydrous hydrogen fluoride.

In carrying out the process of the invention, the aluminum fluoride catalyst may be preformed or preferably prepared in situ by procedures as described above. Hydrogen fluoride and 1,1-dichloroethylene are preferably premixed in the vapor phase and introduced into the first contacting step to pass over or through the aluminum fluoride catalyst at the chosen temperature and pressure. The mixture of hydrogen fluoride and 1,1-dichloroethylene may also contain some inert gas, such as nitrogen, if desired. Depending upon the temperature and the pressure in the first contacting step, the product stream exiting the first contacting step may be in the vapor state or may have some liquid phase. The product stream comprises primarily 1,1-dichloro-1-fluoroethane, unreacted 1,1-dichloroethylene and excess hydrogen fluoride. This first product stream from the first contacting step is introduced into the second contacting step along with any additional hydrogen fluoride, if desired, to pass over or through the aluminum fluoride catalyst. Since the reaction conditions chosen for the second contacting step are such that at least a portion of the first product stream is liquid, the second product stream exiting the second contacting step may be liquid or liquid-vapor mixture whose organic components may comprise about 99.5% 1,1-dichloro-1-fluoroethane, about 0.5% 1-chloro-1,1-difluoroethane and a few hundred parts per million of 1,1-dichloroethylene. The second product stream from the second contacting step may be collected and purified to recover the excess hydrogen fluoride for recycle and to obtain substantially pure 1,1-dichloro-1-fluoroethane. As is known in the art, hydrogen fluoride can be separated by fractional distillation or by cooling and phase-separation from the organic products.

While the above-obtained 1,1-dichloro-1-fluoroethane is satisfactory for most purposes, if pure 1,1-dichloro-1-fluoroethane is desired, the second product stream after removal of hydrogen fluoride can be treated to remove the small amount of 1,1-dichloroethylene present by oxidation of the 1,1-dichloroethylene with aqueous permanganate solutions or by brominating with bromine to convert 1,1-dichloroethylene to a higher boiling dibromo derivative. If desired, 1-chloro-1,1-difluoroethane can be separated from 1,1-dichloro-1-fluoroethane readily by distillation.

The present invention provides a process for 1,1-dichloro-1-fluoroethane offering high yields of and conversion to 1,1-dichloro-1-fluoroethane with substantial reduction of the difficult-to-separate 1,1-dichloroethylene.

Additionally, the 1,1-dichloroethylene content of a mixture of 1,1-dichloroethylene and 1,1-dichloro-1-fluroethane may be reduced by contacting said mixture, optionally with a hydrofluorination catalyst, at an effective temperature and pressure wherein at least some of the mixture is in the liquid state to form a product stream, and recovering 1,1-dichloro-1-fluoroethane with reduced 1,1-dichloroethylene content from the product stream. The conditions and process considerations which may be used for this process are the same as those described above for the second contacting step.

EXAMPLE 1

Two 3-inch internal diameter "Inconel" reactors, 5-feet long, fitted with a gas feed system and external heaters, were filled with about 10 pounds of alumina as 1/16"×¼–⅜" extrudate. The alumina beds were first purged with dry nitrogen while heating to 100° C. The gas feed was switched to a mixture of about 3 pounds per hour (pph) of dry air and 0.1 pph of anhydrous HF. The introduction of the HF caused a temperature rise to about 200° C. to move through the beds. The temperature was stabilized, and additional air/HF mixture was fed to raise the bed temperatures in stages to 300° C. and then to 400° C. The gas feed was switched to HF diluted with dry nitrogen. The nitrogen feed was gradually reduced until pure HF was fed to the beds at between 400°–500° C. The activation took several days.

The so-prepared reactors were connected in series followed by a pressure regulator and then a caustic scrubbing system. The reactor pressures were set at about 45 psig. A mixture of hydrogen fluoride at a rate of 5.0 pph (0.25 pound-mole per hour) and 1,1-dichloroethylene at a rate of 12.2 pph (0.13 pound-mole per hour) (molar HF/1,1-dichloroethylene=1.98) was fed into the first reactor. The temperatures in the first reactor were set at 74° C. at the feed end and was 150° C. at the exit end. The product stream from the first reactor continued on to the second reactor. The temperatures in the second reactor was at 70° C. at the feed end and 51° C. at the exit end. At the pressure of 45 psig used in this example the product mixture at any temperature below about 65° C. is mostly liquid so that more than one-half of the second reactor was filled with liquid. The organic product obtained in this example was 99.5% 1,1-dichloro-1-fluoroethane, 0.5% 1-chloro-1,1-difluoroethane and 600 parts per million (ppm) 1,1-dichloroethylene.

EXAMPLE 2

Using the same equipment and essentially the same reaction conditions as in Example 1, with the exception that the maximum temperature in the first reactor was controlled at 110° C., the residual 1,1-dichloroethylene content in the final product was reduced to 427 ppm.

EXAMPLE 3

Using the reactors as described in Example 1 and a pressure of 40 psig and with a feed rate of 2.6 pound per hour (0.0268 pound-mole) of 1,1-dichloro-ethylene and 1.5 pound per hour (0.075 pound-mole) of hydrogen fluoride (HF/1,1-dichloroethylene of 2.8) and with the entrance temperature of the first reactor set at 150° C. which dropped to about 50° C. before the center of the reactor and down further to 25° C. at the exit end of the first reactor and the second reactor kept at 36° C. for the entire length, the residual 1,1-dichloroethylene in the organic products dropped to 286 ppm. While initial conditions in the first contacting step were vapor phase, at these temperatures and pressures, both reactors were almost completely full of liquid.

EXAMPLE 4

After replacing the first reactor of Example 1 by an "Inconel" reactor 2-inch in diameter and 8-feet long, the system was operated at 40 psig with a feed rate of 9.3 pph (0.096 pound-mole) of 1,1-dichloroethylene and 3.8 pph (0.19 pound mole) of hydrogen fluoride (molar ratio of HF/1,1-dichloroethylene of 2.0), with the maximum temperature of the first reactor at 66° C. which dropped to 32° C. at the exit end, and with the second reactor varying in temperature from 26° C. at the entrance to 8° C. at the exit. Residual 1,1-dichloroethylene was 167 ppm. Initial conditions in the first reactor were vapor phase. Exit conditions in the first reactor were almost completely liquid. Conditions in the second reactor were essentially all liquid.

We claim:

1. A process for preparing 1,1-dichloro-1-fluoroethane comprising the steps of
   (a) contacting a vapor phase mixture of 1,1-dichloroethylene and substantially anhydrous hydrogen fluoride with a hydrofluorination catalyst to produce a first product stream containing 1,1-dichloro-1-fluoroethane and 1,1-dichloroethylene and, thereafter,
   (b) contacting said first product stream with substantially anhydrous hydrogen fluoride in the presence of a hydrofluorination catalyst at an effective temperature and pressure wherein at least some of the first product stream is in the liquid stated to form a second product stream, said temperature being about 5° to about 75° C. and said pressure being about atmospheric to about 80 psig, and
   (c) recovering the second product stream which comprises about 99.5 weight percent 1,1-dichloro-1-fluoroethane and less than 600 ppm 1,1-dichloroethylene.

2. The process of claim 1 wherein the hydrofluorination catalyst is an aluminum fluoride catalyst.

3. The process of claim 1 or 2 wherein the first contacting step is maintained at a temperature of from about 25° C. to about 150° C. and a pressure of from about atmospheric at about 160 psig.

4. The process of claim 3 wherein said mixture of 1,1-dichloroethylene and hydrogen fluoride is a mixture of from about one mole to about fifteen moles of hydrogen fluoride per mole of 1,1-dichloroethylene.

5. The process of claim 3 wherein said temperature in the first contacting step is from about 50° C. to about 100° C., and the temperature in the second contacting step is from about 25° C. to about 75° C.

6. The process of claim 3 wherein said pressure in the first contacting step is from about atmospheric to about 50 psig, and the pressure in the second contacting step is from about 30 psig to about 50 psig.

7. The process of claim 6 wherein said mixture of 1,1-dichloroethylene and hydrogen fluoride is a mixture of from about 1 mole to about 15 moles hydrogen fluoride per mole of 1,1-dichloroethylene.

8. The process of claim 6 wherein said mixture of 1,1-dichloroethylene and hydrogen fluoride is a mixture of from about 1.3 to about 8 moles of hydrogen fluoride per mole of 1,1-dichloroethylene.

9. The process of claim 1 wherein, optionally, additional anhydrous hydrogen fluoride is added to the first product stream prior or during the second contacting step.

10. The process of claim 2 wherein said aluminum fluoride catalyst is an aluminum fluoride prepared by treating anhydrous aluminum chloride or aluminum bromide with hydrogen fluoride.

11. The process of claim 10 wherein said mixture of 1,1-dichloroethylene and hydrogen fluoride is a mixture of from 1.3 to about 2.5 moles of hydrogen fluoride per mole of 1,1-dichloroethylene, said temperature in the first contacting step is from about 50° C. to about 100° C., said temperature in the second contacting step is from about 25° C. to about 75° C., said pressure in the first contacting step is from about atmospheric to about 50 psig and said pressure in the second contacting step is from about 30 psig to about 50 psig.

12. The process of claim 2 wherein said aluminum fluoride catalyst is an aluminum fluoride prepared by treating alumina with hydrogen fluoride.

13. The process of claim 12 wherein said mixture of 1,1-dichloroethylene and hydrogen fluoride is a mixture of from about 1.3 to about 2.5 moles of hydrogen fluoride per mole of 1,1-dichloroethylene, said temperature in the first contacting step is from about 50° C. to about 100° C., said temperature in the second contacting step is from about 25° C. to about 75° C., said pressure in the first contacting step is from about atmospheric to about 50 psig and said pressure in said second contacting step is from about 30 psig to about 50 psig.

14. A process for reducing the 1,1-dichloroethylene content of a mixture of 1,1-dichloroethylene and 1,1-dichloro-1-fluoroethane to about 600 ppm or less comprising providing a feed stream comprising 1,1-dichloroethylene and 1,1-dichloro-1-fluoroethane wherein the 1,1-dichloro-1-fluoroethane is 90 weight percent or greater of the feed stream, contacting said feed stream with substantially anhydrous hydrogen fluoride in the presence of a hydrofluorination catalyst at an effective temperature and pressure wherein at least some of the feed stream is in the liquid state to form a product stream, said temperature being about 5° to about 75° C. and said pressure being about atmospheric to about 80 psig, and recovering the product stream, which comprises about 99.5 weight percent 1,1-dichloro-1-fluoroethane and about 600 ppm or less 1,1-dichloroethylene.

15. The process of claim 14 wherein the hydrofluorination catalyst is an aluminum fluoride catalyst.

16. The process of claim 14 wherein additional hydrogen fluoride is added to the feed stream prior to or during the contacting step.

17. The process of claim 14 wherein said temperature is from about 25° C. to about 75° C.

18. The process of claim 14 wherein said pressure is from about 30 psig to about 50 psig.

19. The process of claim 14 wherein said hydrofluorination catalyst is an aluminum fluoride prepared by treating anhydrous aluminum chloride or aluminum bromide with hydrogen fluoride.

20. The process of claim 14 wherein said hydrofluorination catalyst is an aluminum fluoride prepared by treating alumina with hydrogen fluoride.

21. The process of claim 2 wherein the aluminum fluoride catalyst includes other metal fluorides.

22. The process of claim 15 wherein the aluminum fluoride catalyst includes other metal fluorides.

* * * * *